(12) United States Patent
Wakui

(10) Patent No.: US 11,030,751 B2
(45) Date of Patent: Jun. 8, 2021

(54) CELL IMAGE EVALUATION DEVICE, METHOD, AND PROGRAM

(71) Applicant: FUJIFILM Corporation, Tokyo (JP)

(72) Inventor: Takashi Wakui, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/544,369

(22) Filed: Aug. 19, 2019

(65) Prior Publication Data

US 2019/0370973 A1 Dec. 5, 2019

Related U.S. Application Data

(63) Continuation of application No. PCT/JP2018/011174, filed on Mar. 20, 2018.

(30) Foreign Application Priority Data

Mar. 30, 2017 (JP) .............................. JP2017-067953

(51) Int. Cl.
*G06T 7/11* (2017.01)
*G06T 7/00* (2017.01)
*G06T 7/136* (2017.01)

(52) U.S. Cl.
CPC .............. *G06T 7/11* (2017.01); *G06T 7/0012* (2013.01); *G06T 7/136* (2017.01); *G06T 2207/30024* (2013.01)

(58) Field of Classification Search
CPC ......... G06T 7/11; G06T 7/136; G06T 7/0012; G06T 2207/30024; C12M 41/36
See application file for complete search history.

(56) References Cited

U.S. PATENT DOCUMENTS

| 2013/0064422 A1 | 3/2013 | Ogi | |
| 2013/0095516 A1* | 4/2013 | Myerburg | G01N 21/253 435/29 |

(Continued)

FOREIGN PATENT DOCUMENTS

| JP | 2013-57595 A | 3/2013 |
| JP | 2016-71117 A | 5/2016 |

(Continued)

OTHER PUBLICATIONS

Extended European Search Report dated Feb. 18, 2020, for corresponding European Application No. 18775331.4.

(Continued)

*Primary Examiner* — Jon Chang
(74) *Attorney, Agent, or Firm* — Birch, Stewart, Kolasch & Birch, LLP

(57) ABSTRACT

Provided are a cell image evaluation device, method, and program which are capable of performing more accurate and high reliable evaluation even though a captured image of each part to be observed within a container is an image of which contrast is low due to influence of meniscus. The cell image evaluation device includes a region determination unit that determines whether a captured image obtained by capturing an inside of a container that contains a cell is an image obtained by capturing a meniscus region within the container or an image obtained by capturing a non-meniscus region within the container and an image evaluation unit that evaluates a state of the cell included in the captured image. The image evaluation unit evaluates the image of the meniscus region and the image of the non-meniscus region by different evaluation methods.

20 Claims, 4 Drawing Sheets

(56) References Cited

U.S. PATENT DOCUMENTS

2018/0113294 A1    4/2018  Shiraishi
2018/0164567 A1*   6/2018  Chan .................... G02B 21/367
2018/0307938 A1*  10/2018  Fujimoto ............. G06K 9/6202
2018/0376048 A1*  12/2018  Schurf ..................... G06T 7/60

FOREIGN PATENT DOCUMENTS

JP       2016-127342 A       7/2016
WO    WO 2016/052078 A1     4/2016
WO    WO 2016/104477 A1     6/2016
WO    WO 2017/002458 A1     1/2017

OTHER PUBLICATIONS

International Preliminary Report on Patentability and Written Opinion of the International Searching Authority (Forms PCT/IB/326, PCT/IB/373, and PCT/ISA/237) for International Application No. PCT/JP2018/011174, dated Oct. 10, 2019, with English translation.
International Search Report (Form PCT/ISA/210) for International Application No. PCT/JP2018/011174, dated May 29, 2018, with English translation.
Korean Office Action, dated Feb. 8, 2021, for corresponding Korean Application No. 10-2019-7023860, with an English translation.

* cited by examiner

CELL IMAGE EVALUATION DEVICE, METHOD, AND PROGRAM

CROSS-REFERENCE TO RELATED APPLICATIONS

This application is a Continuation of PCT International Application No. PCT/JP2018/011174 filed on Mar. 20, 2018, which claims priority under 35 U.S.C § 119(a) to Japanese Patent Application No. 2017-067953 filed on Mar. 30, 2017. Each of the above application(s) is hereby expressly incorporated by reference, in its entirety, into the present application.

BACKGROUND OF THE INVENTION

1. Field of the Invention

The present invention relates to a cell image evaluation device, method, and program which evaluate a state of a cell included in a captured image by using the captured image obtained by capturing the cell.

2. Description of the Related Art

Pluripotent stem cells such as embryonic stem (ES) cells and induced pluripotent stem (iPS) cells have ability to differentiate into cells of various tissues, and have received attention as being applicable to regenerative medicine, drug development, and elucidation of diseases.

Meanwhile, a method of evaluating a differentiated state of the cells by capturing the pluripotent stem cells such as the ES cells and the iPS cells or differentiated and induced cells by using a microscope and catching features of an image thereof has been suggested in the related art.

Meanwhile, in order to obtain a high-magnification and wide-field image at the time of capturing the cell by using the microscope as state above, so-called tiling capturing for obtaining has been suggested. Specifically, for example, a method in which parts to be observed within a well are scanned by moving a stage on which a well plate is placed with respect to an image forming optical system, images of the parts to be observed are captured, and then the images of the parts to be observed are connected has been suggested.

SUMMARY OF THE INVENTION

In this case, it has been known that the cell and a liquid such as a culture solution are contained within the well in a case of culturing the cell by using the aforementioned well plate and meniscus is formed on a surface of the liquid.

Particularly, in a case where an image of the cell is captured by using a phase difference microscope device, the influence of the meniscus for the captured image is high, and an image of which contrast is low as compared to a captured image of the non-meniscus region at which the meniscus is not formed.

Accordingly, since an image of each cell is not able to be extracted with high accuracy for the captured image obtained by capturing the meniscus region, for example, in a case where evaluation is performed by using a feature value indicating the state of each cell, accuracy of an evaluation result becomes low, and thus, an evaluation result of which reliability is low may be obtained. That is, in a case where the image of the non-meniscus region and the image of the meniscus region are similarly evaluated, accurate evaluation results may not be able to be obtained.

JP2016-127342A suggests that autofocus control is performed with consideration for meniscus. JP2013-057595A suggests that density correction is performed with consideration for the influence of shadow of a side surface of the well but has not suggested an evaluation method of an image in which contrast of the meniscus region is low.

The present invention has been made in view of the aforementioned problems, and an object of the present invention is to provide a cell image evaluation device, method, and program which are capable of performing more accurate and high reliable evaluation even though a captured image of each part to be observed within a container is an image of which contrast is low due to influence of meniscus.

A cell image evaluation device according to an aspect of the present invention comprises a region determination unit that determines whether a captured image obtained by capturing an inside of a container that contains a cell is an image obtained by capturing a meniscus region within the container or an image obtained by capturing a non-meniscus region within the container, and an image evaluation unit that evaluates a state of the cell included in the captured image. The image evaluation unit evaluates the image of the meniscus region and the image of the non-meniscus region by different evaluation methods.

In the cell image evaluation device according to the aspect of the present invention, the region determination unit may determine whether the captured image is the image of the meniscus region or the image of the non-meniscus region based on a feature value of the captured image.

In the cell image evaluation device according to the aspect of the present invention, the region determination unit may determine whether the captured image is the image of the meniscus region or the image of the non-meniscus region based on preset positional information within the container.

In the cell image evaluation device according to the aspect of the present invention, the region determination unit may determine whether the captured image is the image of the meniscus region or the image of the non-meniscus region based on a feature value of the captured image and preset positional information within the container.

In the cell image evaluation device according to the aspect of the present invention, the image evaluation unit may evaluate the image of the non-meniscus region by using a feature value indicating the state of the cell included in the captured image, and may evaluate the image of the meniscus region by using an image feature value.

In the cell image evaluation device according to the aspect of the present invention, the feature value indicating the state of the cell may include at least one of a feature value of a state of each cell, a feature value of nucleolus included in the cell, a feature value of white streaks, a feature value of nucleus included in the cell, or a nucleocytoplasmic ratio (NC ratio) of the cell.

In the cell image evaluation device according to the aspect of the present invention, the image evaluation unit may integrate an evaluation result of the image of the meniscus region within the container and an evaluation result of the image of the non-meniscus region within the container to calculate an evaluation result for the container.

In the cell image evaluation device according to the aspect of the present invention, the image evaluation unit may add weights to the evaluation result of the image of the meniscus region and the evaluation result of the image of the non-meniscus region in a case of calculating the evaluation result for the container.

In the cell image evaluation device according to the aspect of the present invention, the weight to be added to the evaluation result of the image of the non-meniscus region may be larger than the weight to be added to the evaluation result of the image of the meniscus region.

In the cell image evaluation device according to the aspect of the present invention, the captured image may be an image obtained by capturing each part to be observed within the container by moving at least one of a stage on which the container is placed or an image forming optical system that forms an image of the cell within the container, and the region determination unit may determine whether the captured image of each part to be observed is the image of the meniscus region or the image of the non-meniscus region.

In the cell image evaluation device according to the aspect of the present invention, the region determination unit may determine whether the captured image is an image obtained by capturing a rippling region of a liquid within the container, and the image evaluation unit may evaluate the image obtained by capturing the rippling region by the same evaluation method as an evaluation method of evaluating the image of the meniscus region.

A cell image evaluation method according to another aspect of the present invention comprises determining whether a captured image obtained by capturing an inside of a container that contains a cell is an image obtained by capturing a meniscus region within the container or an image obtained by capturing a non-meniscus region within the container, and evaluating the image of the meniscus region and the image of the non-meniscus region by different evaluation methods in a case of evaluating a state of the cell included in the captured image.

A cell image evaluation program according to still another aspect of the present invention causes a computer to function as a region determination unit that determines whether a captured image obtained by capturing an inside of a container that contains a cell is an image obtained by capturing a meniscus region within the container or an image obtained by capturing a non-meniscus region within the container, and an image evaluation unit that evaluates a state of the cell included in the captured image. The image evaluation unit evaluates the image of the meniscus region and the image of the non-meniscus region by different evaluation methods.

In accordance with the cell image evaluation device, method, and program according to the embodiment of the present invention, it is determined whether the captured image obtained by capturing the inside of the container that contains the cell is the image obtained by capturing the meniscus region within the container or the image obtained by capturing the non-meniscus region, and the image of the meniscus region and the image of the non-meniscus region are evaluated by different evaluation methods in a case of evaluating the state of the cell included in the captured image. Accordingly, it is possible to perform more accurate and high reliable evaluation by evaluating the image by the evaluation method suitable for the image even though the image of the meniscus region is the image of which contrast is low due to influence of meniscus.

DESCRIPTION OF THE PREFERRED EMBODIMENTS

Figure 1:
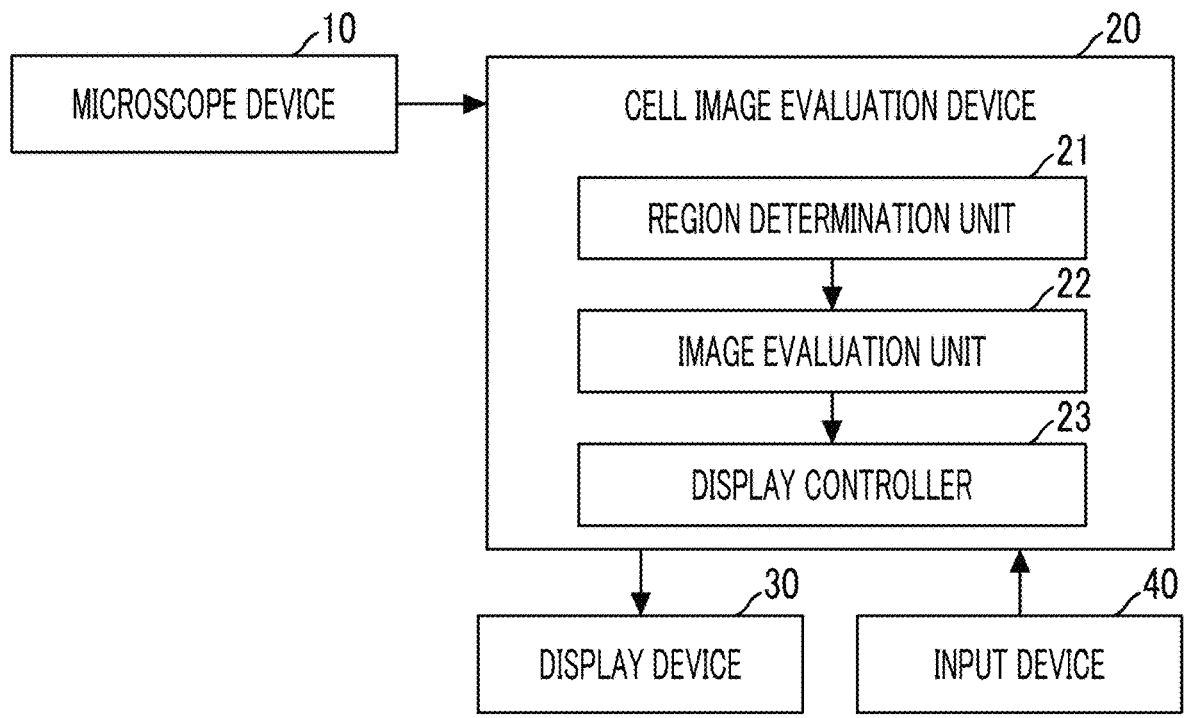
FIG. 1 is a block diagram showing a schematic configuration of a cell image evaluation device according to an embodiment of the present invention.

Hereinafter, a cell image evaluation system using embodiments of a cell image evaluation device, method, and program according to an embodiment of the present invention will be described in detail with reference to the drawings. FIG. 1 is a block diagram showing a schematic configuration of the cell image evaluation system according to the embodiment of the present invention.

As shown in FIG. 1, the cell image evaluation system according to the present embodiment comprises a microscope device 10, a cell image evaluation device 20, a display device 30, and an input device 40.

The microscope device 10 captures cells contained in a culture container, and outputs a captured image. In the present embodiment, specifically, a phase difference microscope device comprising an imaging element such as a charge-coupled device (CCD) image sensor or a complementary metal-oxide semiconductor (CMOS) image sensor is used. As the imaging element, an imaging element in which red, green, and blue (RGB) color filters are provided may be used, or a monochrome imaging element may be used. A phase difference image of the cells contained in the culture container is formed on the imaging element, and the phase difference image is output as the captured image from the imaging element. The microscope device 10 is not limited to the phase difference microscope device, and other microscope devices such as a differential interference microscope device and a bright-field microscope device may be used.

The capturing targets may be a cell colony in which a plurality of cells is aggregated or a plurality of cells which is dispersedly distributed. The cells as the capturing targets are cells of the captured pluripotent stem cells such as iPS cells and ES cells, cells of nerve, skin, cardiac muscle, and liver differentiated and induced from stem cells, and cells and cancer cells of organs obtained from the human body.

In the present embodiment, a well plate with multiple wells is used as the culture container. In a case where the well plate is used, each well corresponds to the container according to the embodiment of the present invention. The microscope device 10 comprises a stage at which the well plate is provided. The stage moves in an X direction and a Y direction perpendicular within a horizontal plane. Parts to be observed within the wells of the well plate are scanned due to the movement of the stage, and thus, cell images for the parts to be observed are captured. The captured image of each part to be observed is output to the cell image evaluation device 20.

Figure 2:
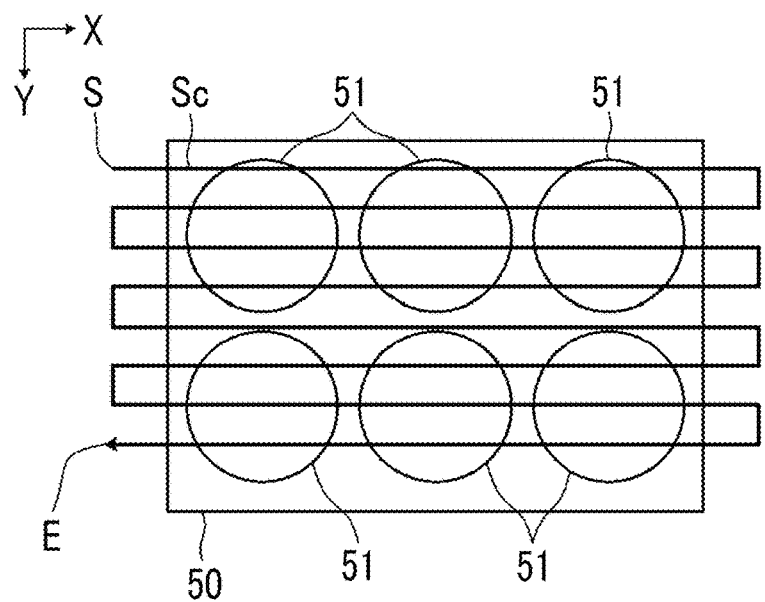
FIG. 2 is a diagram showing a scanning locus of each part to be observed in a well plate.

FIG. 2 is a diagram showing an example in which a scanning locus of each part to be observed is expressed by using a solid line Sc in a case where a well plate 50 having six wells 51 is used. As shown in FIG. 2, each part to be observed within the well plate 50 is scanned along a solid line Sc from a scanning start point S to a scanning end point E due to the movement of the stage in the X direction and the Y direction.

Although it has been described in the present embodiment that the captured image of each part to be observed within the well is captured by moving the stage, the present invention is not limited thereto. The captured image of each part observed may be captured by moving an image forming optical system that forms a phase difference image of the cell on the imaging element toward the stage. Alternatively, both the stage and the image forming optical system may move.

Although the well plate is used in the present embodiment, the container in which the cell is contained is not limited thereto. For example, other containers such as petri dishes or dishes may be used.

As shown in FIG. 1, the cell image evaluation device 20 comprises a region determination unit 21, an image evaluation unit 22, and a display controller 23. The cell image evaluation device 20 is a computer comprising a central processing unit, a semiconductor memory, and a hard disk, and an embodiment of a cell image evaluation program according to the present invention is installed in a hard disk. The cell image evaluation program is executed by the central processing unit, and thus, the region determination unit 21, the image evaluation unit 22, and the display controller 23 shown in FIG. 1 function. Although it has been described in the present embodiment that the functions of the units are performed by the cell image evaluation program, the present invention is not limited thereto. For example, the functions of the units may be performed by appropriately combining a plurality of integrated circuits (ICs), a processor, an application specific integrated circuit (ASIC), a field-programmable gate array (FPGA), and a memory. The cell image evaluation program may be stored in a non-transitory computer-readable recording medium, and may be read into a computer constituting the cell image evaluation device 20. The cell image evaluation program may be distributed via a network.

Figure 3:
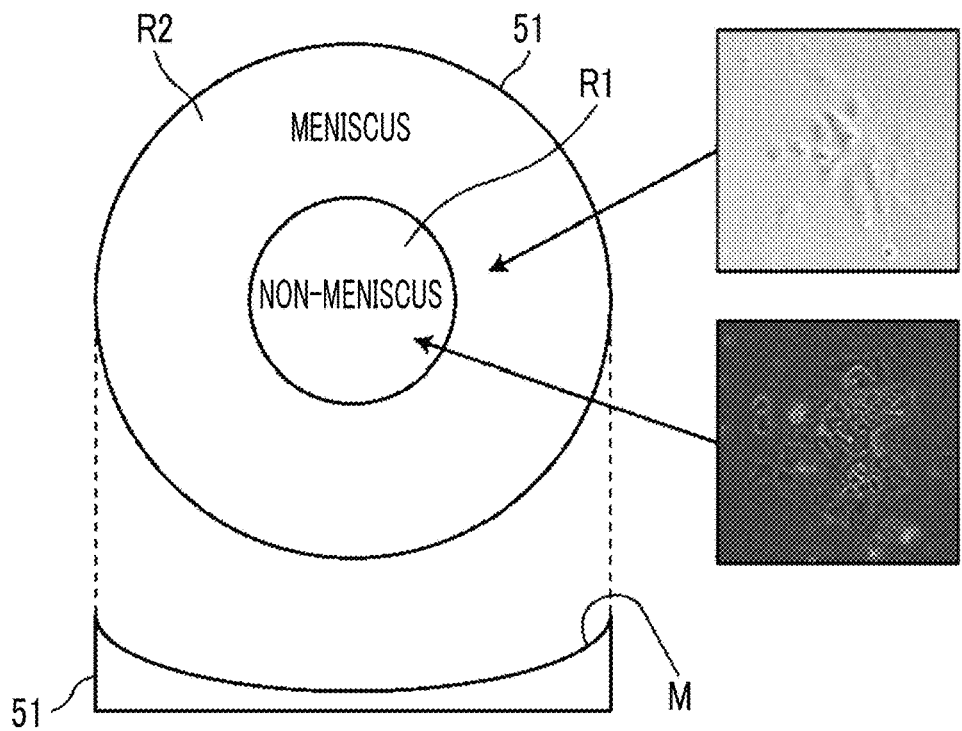
FIG. 3 shows a side sectional view and a top view of the well.
Figure 4:
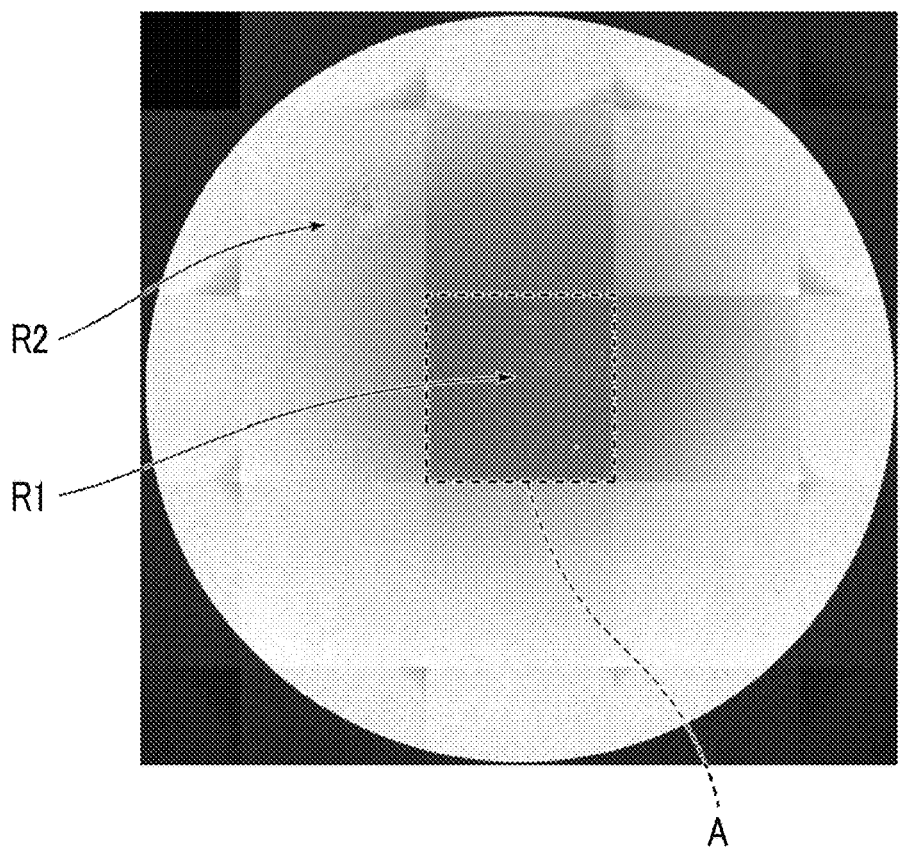
FIG. 4 is a diagram showing an example of a captured image of each part to be observed within the well.

The region determination unit 21 determines whether the captured image of each part to be observed which is captured by the microscope device 10 is an image obtained by capturing a meniscus region within the well or a non-meniscus region. FIG. 3 shows a side sectional view and a top view of the well 51. FIG. 4 is a diagram showing an example of the captured image of each part to be observed within the well. In FIG. 4, each divided region A in a rectangular region corresponds to each part to be observed.

The cells and a liquid such as a culture solution are contained within the well 51, but a meniscus M is formed on a surface of the liquid as shown in FIG. 3. As shown in FIGS. 3 and 4, an image obtained by capturing a non-meniscus region R1 is a high-contrast image, but an image obtained by capturing a meniscus region R2 is a low-contrast image. Accordingly, since it is not possible to extract images of individual cells with high accuracy for the image of the meniscus region R2, in a case where the evaluation is performed by using, for example, a feature value indicating a state of each cell, the accuracy of an evaluation result becomes low, and thus, the reliability of the evaluation result may also be low. In a case where the image of the non-meniscus region and the image of the meniscus region are evaluated by the same evaluation method, it may be difficult to obtain an accurate evaluation result. The influence of the meniscus region becomes high as the container becomes smaller. For example, in a case where the well plate has six wells, a rage having a radius of 60% or more from a center of each well is the meniscus region. In a case where the well plate has 24 wells, a range having a radius of 25% or more from the center of the well is the meniscus region.

In the cell image evaluation system of the present embodiment, the region determination unit 21 determines whether the captured image of each part to be observed is the image of the meniscus region or the non-meniscus region, and changes the evaluation method according to the determination result.

Specifically, the region determination unit 21 calculates the feature value of the captured image of each part to be observed, and determines whether the captured image is the image of the meniscus region or the image of the non-meniscus region based on the feature value. For example, the contrast and luminance of the captured image can be used as the feature value of the captured image. In a case where the determination is performed by using the contrast of the captured image, the region determination unit 21 may determine that the captured image of which the contrast is equal to or greater than a threshold value is the image of the non-meniscus region, and may determine that the captured image of which the contrast is less than the threshold value is the image of the meniscus region. In a case where the determination is performed by using the luminance of the captured image, the region determination unit 21 may determine that the captured image of which the luminance is less than a threshold value is the image of the non-meniscus region, and may determine that the captured image of which the luminance is equal to or greater than the threshold value is the image of the meniscus region. The luminance mentioned herein may be an average of the luminances of the captured image, or may be a maximum value or a median value.

The image evaluation unit 22 obtains the captured image of each part to be observed, and evaluates the state of the cell included in the captured image. For example, a case where the state of the cell is evaluated means that the image evaluation unit 22 evaluates whether the cells included in the captured image are undifferentiated cells or differentiated cells, counts the number of cells for each kind of the cell in a case of co-culturing, evaluates percentages of the undifferentiated cells and the differentiated cells included in the captured image, evaluates a growth rate of the cell or the cell colony, or evaluates a reduction rate of cancer cells by anticancer drugs. Here, the evaluation of the state of the cell is not limited thereto, and other evaluation methods may be used.

The image evaluation unit 22 evaluates the state of the cell by different evaluation methods for the image of the meniscus region and the image of the non-meniscus region. Specifically, the image evaluation unit 22 evaluates the image of the non-meniscus region by using the feature value indicating the state of the cell included in the captured image, and evaluates the image of the meniscus region by using an image feature value. The feature value indicating the state of the cell and the image feature value will be described below.

The image evaluation unit 22 of the present embodiment integrates the evaluation result of the image of the meniscus region and the evaluation result of the image of the non-meniscus region within the well, and calculates the evaluation result for the well. That is, the evaluation result of each well is calculated. It is possible to manage the cells of each well in a case of passaging or shipping of the cells by calculating the evaluation result of each well (each container) as stated above.

Specifically, for example, the percentage of the differentiated cells and the percentage of the undifferentiated cells for each well may be obtained by calculating average values of the percentages of the differentiated cells and the percentages of the undifferentiated cells included in the captured images of the parts to be observed within the well.

Alternatively, in a case where the growth rate of the cell or the cell colony is evaluated for the captured image of each part to be observed within the well, an average value of the growth rates of the part to be observed may be obtained as a growth rate of each well. A percentage of the number of parts to be observed, of which the growth rate is equal to or greater than a threshold value, to the number of all parts to be observed within the well may be calculated, and this percentage may be obtained as the growth rate of each well. Alternatively, the evaluation result of each well may be "good" in a case where this percentage is equal to or greater than the threshold value, and the evaluation result of each well may be "poor" in a case where this percentage is less than the threshold value. Alternatively, the evaluation result of the part to be observed, of which the growth rate is equal to or greater than the threshold value, may be "good", and the evaluation result of the part to be observed, of which the growth rate is less than the threshold value, may be "poor". Further, the evaluation result of each well may be "good" in a case where the number of parts to be observed, of which the evaluation result is "good" is equal to or greater than a threshold value, and the evaluation result of each well may be "poor" in a case where the number of parts to be observed of which the evaluation result is "good" is less than the threshold value.

Figure 5:
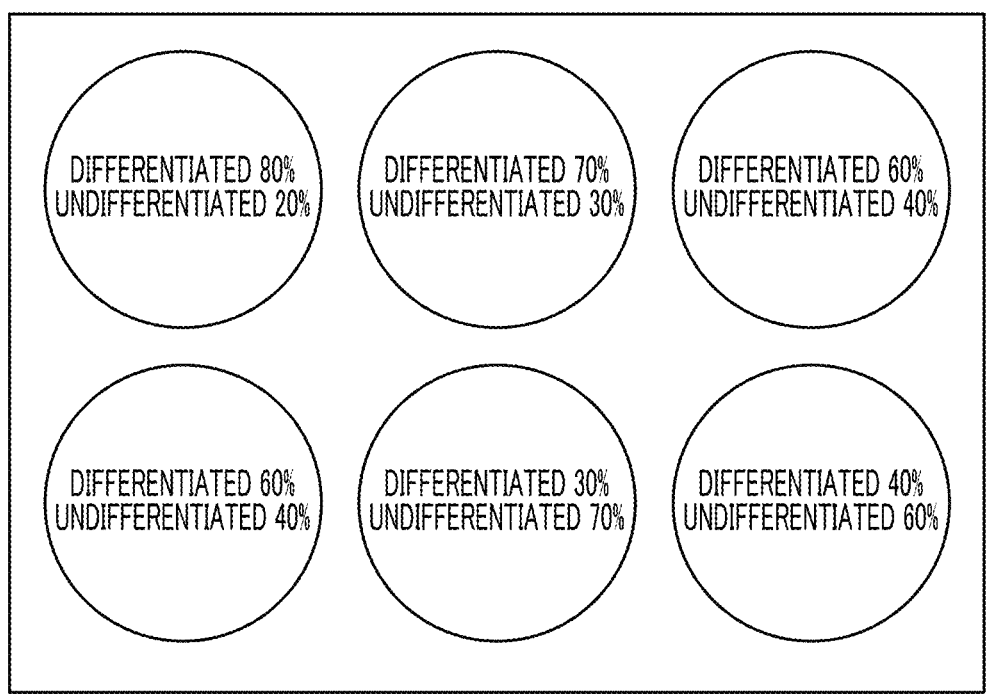
FIG. 5 is a diagram showing a display example of an evaluation result integrated for the wells.

The display controller 23 displays the evaluation result using the image evaluation unit 22 on the display device 30. Specifically, in the present embodiment, since the evaluation result of each well is calculated by the image evaluation unit 22, the display controller 23 displays the evaluation result of each well on the display device 30. FIG. 5 shows an example in which the percentage of the differentiated cells and the percentage of the undifferentiated cells of each well are calculated and the calculation result is displayed as the integrated evaluation result in a case where the well plate has six wells. In the example of FIG. 5, 80% of differentiated cells and 20% of undifferentiated cells are present in an upper left well. 70% of differentiated cells and 30% of undifferentiated cells are present in an upper central well. 60% of differentiated cells and 40% of undifferentiated cells are present in an upper right well. 60% of differentiated cells and 40% of undifferentiated cells are present in a lower left well. 30% of differentiated cells and 70% of undifferentiated cells are present in a lower central well. 40% of differentiated cells and 60% of undifferentiated cells are present in a lower right well.

The display controller 23 generates a combination image by connecting the captured images of the parts to be observed, and displays the combination image on the display device 30.

The display device 30 displays the evaluation result using the image evaluation unit 22 and the combination image generated by the display controller 23 as stated above, and comprises, for example, a liquid crystal display. The display device 30 may be a touch panel, and may also serve as the input device 40.

The input device 40 comprises a mouse or a keyboard, and receives various setting inputs from the user.

Next, the feature value indicating the state of the cell and the image feature value will be described. At least one of a feature value of state of each cell, a feature value of a nucleolus included in the cell, a feature value of white streaks, a feature value of nucleus included in the cell, or a NC ratio of the cell can be used as the feature value indicating the state of the cell.

Examples of the feature value indicating the state of each cell include the number of cells, the density of cells, an increasing rate of the cells, and a degree of circularity of the cell. However, other feature values may be used as long as each cell included in the captured image is recognized and a feature value is calculated based on the recognized cell. Examples of the method of recognizing the cell included in the captured image include a method of detecting an edge of the image of the cell, a method of detecting the cell by using a pattern matching process, a method of detecting the cell by using a discriminator generated by machine learning. However, other known methods can be used. As for the degree of circularity of the cell, the degree of circularity of the undifferentiated cell becomes relatively high, but the degree of circularity of the differentiated cell becomes relatively low since the differentiated cell has an elongated shape. Accordingly, the image evaluation unit can evaluate whether the cells are the differentiated cells or the undifferentiated cells by calculating the degrees of circularity of each cell. In the pluripotent stem cells, in a case where the cell differentiates, since a chromatin structure in the nucleus changes and becomes dark, it is possible to evaluate whether the cell differentiates or undifferentiates by detecting the nucleus and then evaluating luminance of the nucleus. Here, the method of evaluating whether the cells are the differentiated cells or the undifferentiated cells is not limited thereto, and other known methods can be used.

Examples of the feature value of the nucleus or nucleolus included in the cell include the number of nuclei or nucleoli, the density of nuclei or nucleoli, and an increasing rate of the nuclei or nucleoli. However, other feature values may be used as long as the nuclei or nucleoli included in the captured image is recognized and a feature value is calculated based on the recognized nuclei or nucleoli. Similarly to the method of recognizing the cell, the edge detection, the detection using the pattern matching, and the detection using the discriminator can be used as the method of recognizing the nuclei or nucleoli included in the captured image.

The white streaks are blurring (halo) of light due to diffracted light generated between the cells and a background. Examples of the feature value of the white streaks include the total area of white streaks, the density of white streaks, and the distribution state of white streaks. However, other feature values may be used as long as the white streaks included in the captured image are recognized and a feature value is calculated based on the recognized white streaks. As the method of recognizing the white streaks, for example, the captured image may be binarized, and the white streaks may be extracted through threshold value processing. Alternatively, a method of detecting the white streaks by using the pattern matching process, a method of detecting the white streaks by using discriminator generated by machine learning, or other known methods may be used as the method of recognizing the white streaks. As for the feature value of the white streaks, for example, the amount of white streaks is small in a state in which the number of undifferentiated cells is large within the cell colony, but the number of white streaks is large in a case where the differentiation progresses and the number of differentiated cells is large. Accordingly, it is possible to evaluate a degree of differentiation or a degree of undifferentiation of the cell colony or a growth rate of the cell colony based on the feature value of the white streaks.

The NC ratio of the cell is an area ratio of the nucleus to the cytoplasm. It is possible to obtain the NC ratio by using detectors of the cytoplasm and the nucleus. In general, the cytoplasm has a gray and flat appearance, whereas the nucleus is relatively round and includes a structure such as the nucleolus therein. Accordingly, a cytoplasm region and a nucleus region are obtained by creating the detectors through machine learning and applying the created detectors to the captured image. It is possible to calculate the NC ratio by calculating an area ratio of the cytoplasm region and the nucleus region obtained in this manner. The NC ratio may be calculated for each cell colony, or the NC ratio within a previously designated region.

Meanwhile, the image feature value used in a case of evaluating the image of the meniscus region is a feature value of the captured image itself. Specifically, an average luminance of the captured image, a variance of the luminance of the captured image, a difference between a maximum value and a minimum value of the luminance of the captured image, contrast of the captured image, entropy of the captured image, a spatial frequency distribution of the captured image, directivity of the captured image, and a Zernike feature of the captured image may be used. In a case where the image feature value is used in a case of evaluating the image of the meniscus region, since the contrast of the image of the meniscus region is low as stated above, detection accuracy of the image of each cell or the image of the nucleolus becomes low. Accordingly, evaluation accuracy in a case where the evaluation is performed by using the image feature value of the captured image itself is more improved than evaluation accuracy in a case where the evaluation is performed by using the feature value indicating the state of each cell like the image of the non-meniscus region.

As the method of evaluating the state of the cell included in the captured image by using such an image feature value, for example, a relationship between the image feature value and the evaluation result corresponding to the image feature value may be obtained in advance through an experiment, and the evaluation result may be obtained based on the relationship between the image feature value of the captured image and the evaluation result. An evaluator may be generated by learning the relationship between the image feature value and the evaluation result corresponding to the image feature value through, for example, machine learning, and the evaluation result may be obtained by inputting the image feature value of the captured image to the evaluator.

Figure 6:
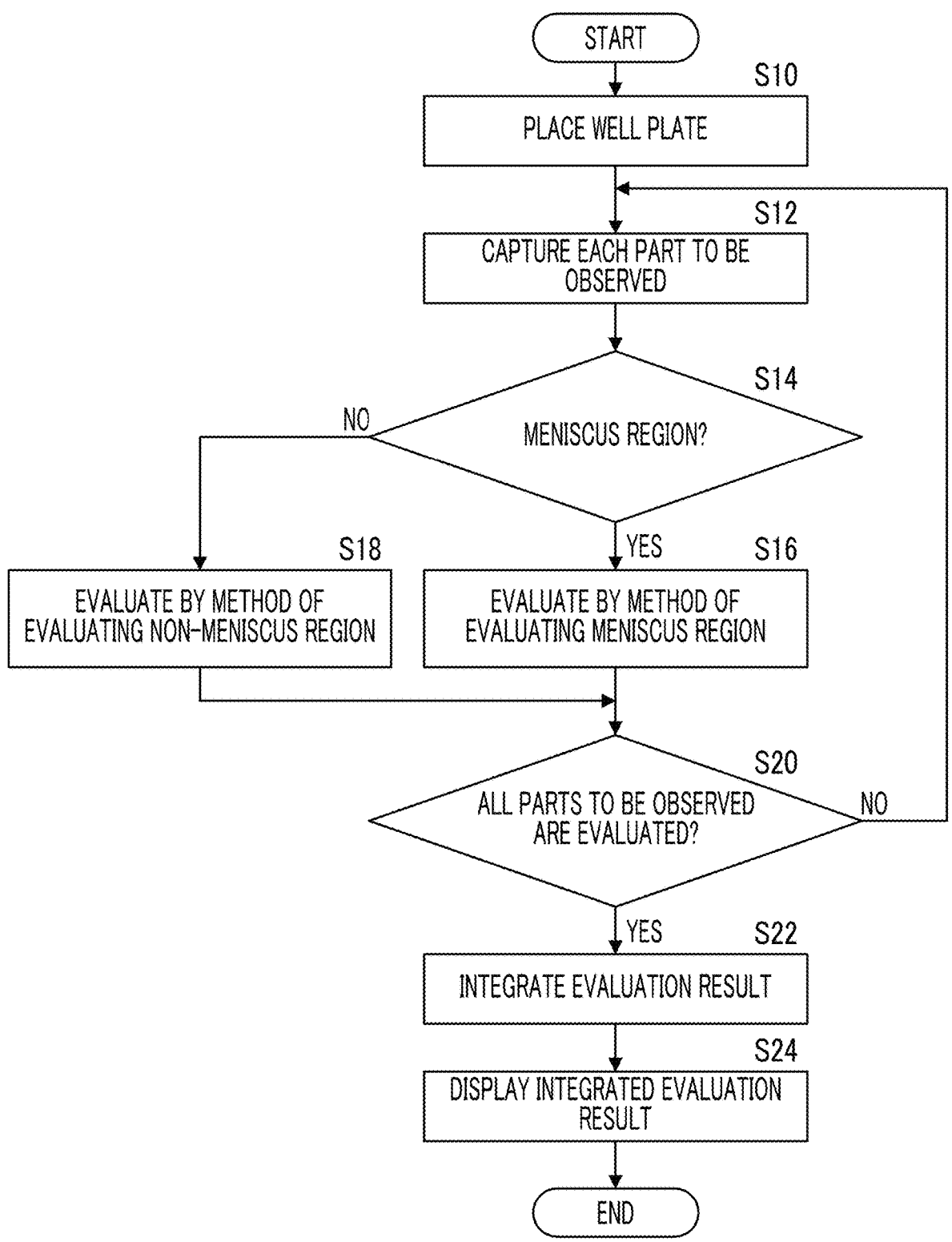
FIG. 6 is a flowchart for describing an operation of the cell image evaluation system using the cell image evaluation device according to the embodiment of the present invention.

Next, an operation of the cell image evaluation system of the present embodiment will be described with reference to a flowchart shown in FIG. 6.

Initially, the well plate that contains the cells and the culture solution is placed on the stage of the microscope device 10 (S10). The parts to be observed within each well of the well plate are scanned while moving the stage in the X direction and the Y direction, and thus, the captured images of the parts to be observed are captured (S12).

The captured images of the parts to be observed which are captured in the microscope device 10 are sequentially output to the cell image evaluation device 20, and are sequentially input to the region determination unit 21 and the display controller 23 (S12). The region determination unit 21 determines whether the input captured image of the part to be observed is the image of the meniscus region or the image of the non-meniscus region (S14).

In a case where the region determination unit 21 determines that the captured image is the image of the meniscus region, the image evaluation unit 22 evaluates the captured image by using the method of evaluating the image of the meniscus region (S16). Specifically, the image feature value is calculated for the captured image, and the state of the cell included in the captured image is evaluated by using the image feature value.

Meanwhile, in a case where the region determination unit 21 determines that the captured image is the image of the non-meniscus region, the image evaluation unit 22 evaluates the captured image by using the method of evaluating the image of the non-meniscus region (S18). Specifically, the feature value indicating the state of the cell is calculated for the captured image, and the state of the cell included in the captured image is evaluated by using the feature value.

The processing of S12 to S18 is repeated until all the parts to be observed are scanned and the evaluation of the captured images of all the parts to be observed is ended (S20, NO).

In a case where the evaluation of the captured images of all the parts to be observed is ended (S20, YES), the image evaluation unit 22 integrates the evaluation results of the captured images of the parts to be observed, and obtains the evaluation result of each well (S22).

The display controller 23 generates the combination image by using the captured images of the parts to be observed, displays the combination image on the display device 30, and displays the integrated evaluation result of each well on the display device 30 (S24).

According to the cell image evaluation system of the embodiment, since it is determined whether the captured image of each part to be observed is the image obtained by capturing the meniscus region or the image obtained by capturing the non-meniscus region within the container and the evaluation is performed by different evaluation methods for the image of the meniscus region and the image of the non-meniscus region in a case of evaluating the state of the cell included in the captured image, even though the image of the meniscus region is the image of which the contrast is low due to the influence of the meniscus, it is possible to perform more accurate and high reliable evaluation by performing the evaluation by the evaluation method suitable for the image.

Although it has been described in the embodiment that the image evaluation unit 22 integrates the evaluation result of the image of the meniscus region and the evaluation result of the image of the non-meniscus region within the well, weights may be added to the evaluation result of the image of the meniscus region and the evaluation result of the image of the non-meniscus region in a case of calculating the evaluation result integrated in this manner. As for the weight, it is preferable that a weight to be added to the evaluation result of the image of the non-meniscus region is set so as to be larger than a weight to be added to the evaluation result of the image of the meniscus region. This is because it is considered that the accuracy of the evaluation result is high since the image of the non-meniscus region is less influenced by the meniscus and is the image of which the contrast is high.

Specifically, in a case where the average value of the growth rates of the parts to be observed within the well is obtained as the growth rate of each well, a weight of less than 0.5 may be added to the growth rate of the part to be observed of the meniscus region, and a weight of 0.5 or more may be added to the growth rate of the part to be observed of the non-meniscus region.

Alternatively, in a case where the evaluation result of the part to be observed, of which the growth rate is equal to or greater than the threshold value, is "good" and the evaluation result of the part to be observed, of which the growth rate is less than the threshold value, is "poor", the image may be evaluated as "good" or "poor" by adding the weight of less than 0.5 to the growth rate of the part to be observed of the meniscus region, and the image may be evaluated as "good" or "poor" by adding the weight of 0.5 or more to the growth rate of the part to be observed of the non-meniscus region. As stated above, the evaluation result of each well may be "good" in a case where the number of parts to be observed, which are included in the well and of which the evaluation result is "good", is equal to or greater than the threshold value, and the evaluation result of each well may be "poor" in a case where the number of parts to be observed, of which the evaluation result is "good", is less than the threshold value.

Although it has been described in the embodiment that it is determined whether the captured image is the image of the meniscus region or the image of the non-meniscus region based on the feature value such as the contrast of the captured image, the determination method is not limited thereto. It may be determined whether the captured image is the image of the meniscus region or the image of the non-meniscus region based on preset positional information within the well.

As stated above, the range of the meniscus formed within the well can be known in advance depending on the size of the well. Accordingly, it may be determined whether the captured image is the image of the meniscus region or the image of the non-meniscus region depending on whether or not the position of the part to be observed in which the captured image is captured within the well corresponds to a peripheral portion of the well. Alternatively, it may be determined whether or not the captured image is the image of the meniscus region based on the feature value such as the contrast of the captured image as in the embodiment, and it may be determined that the captured image is the image of the meniscus region in a case where it is determined that the captured image is the image of the meniscus region and the position of the part to be observed within the well corresponds to the peripheral portion of the well.

Specifically, a table in which the positional information of the part to be observed within the well and region specification information indicating whether the captured image is the meniscus region or the non-meniscus region are associated with each other may be set in advance. In a case of capturing the captured image of any part to be observed within the well, the region specification information associated with the positional information of the part to be observed may be obtained while referring to the table, and the region specification information and the captured image may be stored in association with each other. In a case of performing the determination using the region determination unit 21, the region specification information associated with the captured image may be referred to.

As for the positional information of the part to be observed within the well, for example, a relationship between positional information of the stage and the positional information of the part to be observed within the well may be set in advance, and the positional information of the part to be observed may be obtained based on the positional information of the stage. Alternatively, the image of the entire well plate may be calculated, the position of the well within the image may be calculated through the edge detection, and the positional information of the part to be observed within the well may be obtained based on the positional information of the well.

As stated above, the range of the meniscus formed within the well varies depending on the number of wells of the well plate. In a case where another culture container as well as the well plate is used, the range of the meniscus varies depending on the kind of the culture container.

Accordingly, the table in which the positional information of the part to be observed within the culture container and the region specification information are associated with each other may be set for each kind of the culture container. The user may set and input information of the kind of the culture container by using the input device 40, and may use the table corresponding to the kind thereof. The user may not set and input the information of the kind of the culture container. Identification information such as a barcode may be added to the culture container, and the identification information may be read out and obtained.

As stated above, it may be determined whether the captured image is the image of the meniscus region or the image of the non-meniscus region based on the positional information of the part to be observed within the well, a region of "rippling" of the culture solution may be determined based on the feature value such as the contrast of the captured image, and the rippling region may be evaluated by the same evaluation method as the meniscus region. The "rippling" of the culture solution is formed on the surface of the culture solution, and may be generated in a case where the position within the well is out of the peripheral portion of the well. Since an optical phenomenon is similar to that of the meniscus region, it is possible to obtain a more appropriate evaluation result by evaluating the image by the same evaluation method as the meniscus region.

EXPLANATION OF REFERENCES

10: microscope device
20: cell image evaluation device
21: region determination unit
22: image evaluation unit
23: display controller
30: display device
40: input device
50: well plate
51: well
A: region (part to be observed)
E: scanning end point
M: meniscus
Sc: solid line indicating scanning locus
R1: non-meniscus region
R2: meniscus region
S: scanning start point

What is claimed is:

1. A cell image evaluation device comprising
a processor which is configured to
determine whether a captured image obtained by capturing an inside of a container that contains a cell with an image capturing device is an image obtained by capturing a meniscus region within the container or an image obtained by capturing a non-meniscus region within the container; and
evaluate a state of the cell included in the captured image,
wherein the processor is further configured to evaluate the image of the meniscus region and the image of the non-meniscus region by different evaluation methods.

2. The cell image evaluation device according to claim 1,
wherein the processor is further configured to determine whether the captured image is the image of the meniscus region or the image of the non-meniscus region based on a feature value of the captured image.

3. The cell image evaluation device according to claim 1, wherein the processor is further configured to determine whether the captured image is the image of the meniscus region or the image of the non-meniscus region based on information regarding a preset position within the container.

4. The cell image evaluation device according to claim 1, wherein the processor is further configured to determine whether the captured image is the image of the meniscus region or the image of the non-meniscus region based on a feature value of the captured image and information regarding a preset position within the container.

5. The cell image evaluation device according to claim 1, wherein the processor is further configured to evaluate the image of the non-meniscus region by using a feature value indicating the state of the cell included in the captured image, and evaluates the image of the meniscus region by using an image feature value.

6. The cell image evaluation device according to claim 2, wherein the processor is further configured to evaluate the image of the non-meniscus region by using a feature value indicating the state of the cell included in the captured image, and evaluates the image of the meniscus region by using an image feature value.

7. The cell image evaluation device according to claim 3, wherein the processor is further configured to evaluate the image of the non-meniscus region by using a feature value indicating the state of the cell included in the captured image, and evaluates the image of the meniscus region by using an image feature value.

8. The cell image evaluation device according to claim 4, wherein the processor is further configured to evaluate the image of the non-meniscus region by using a feature value indicating the state of the cell included in the captured image, and evaluates the image of the meniscus region by using an image feature value.

9. The cell image evaluation device according to claim 5, wherein the feature value indicating the state of the cell includes at least one of a feature value of a state of each cell, a feature value of a nucleolus included in the cell, a feature value of white streaks, a feature value of a nucleus included in the cell, or a nucleocytoplasmic ratio of the cell.

10. The cell image evaluation device according to claim 6, wherein the feature value indicating the state of the cell includes at least one of a feature value of a state of each cell, a feature value of a nucleolus included in the cell, a feature value of white streaks, a feature value of a nucleus included in the cell, or a nucleocytoplasmic ratio of the cell.

11. The cell image evaluation device according to claim 7, wherein the feature value indicating the state of the cell includes at least one of a feature value of a state of each cell, a feature value of a nucleolus included in the cell, a feature value of white streaks, a feature value of a nucleus included in the cell, or a nucleocytoplasmic ratio of the cell.

12. The cell image evaluation device according to claim 8, wherein the feature value indicating the state of the cell includes at least one of a feature value of a state of each cell, a feature value of a nucleolus included in the cell, a feature value of white streaks, a feature value of a nucleus included in the cell, or a nucleocytoplasmic ratio of the cell.

13. The cell image evaluation device according to claim 1, wherein the processor is further configured to integrate an evaluation result of the image of the meniscus region within the container and an evaluation result of the image of the non-meniscus region within the container to calculate an evaluation result for the container.

14. The cell image evaluation device according to claim 2, wherein the processor is further configured to integrate an evaluation result of the image of the meniscus region within the container and an evaluation result of the image of the non-meniscus region within the container to calculate an evaluation result for the container.

15. The cell image evaluation device according to claim 13, wherein the processor is further configured to add a weight to the evaluation result of the image of the meniscus region and a weight to the evaluation result of the image of the non-meniscus region to calculate the evaluation result for the container.

16. The cell image evaluation device according to claim 15, wherein the weight to be added to the evaluation result of the image of the non-meniscus region is larger than the weight to be added to the evaluation result of the image of the meniscus region.

17. The cell image evaluation device according to claim 1, wherein the captured image is an image obtained by capturing at least one part to be observed within the container by moving at least one of a stage on which the container is placed or an image forming optical system that forms an image of the cell within the container, and the processor is further configured to determine whether the captured image of each of the at least one part to be observed is the image of the meniscus region or the image of the non-meniscus region.

18. The cell image evaluation device according to claim 1, wherein the processor is further configured to determine whether the captured image is an image obtained by capturing a rippling region of a liquid within the container, and evaluate the image obtained by capturing the rippling region by the same evaluation method as an evaluation method of evaluating the image of the meniscus region.

19. A cell image evaluation method comprising:
determining whether a captured image obtained by capturing an inside of a container that contains a cell is an image obtained by capturing a meniscus region within the container or an image obtained by capturing a non-meniscus region within the container; and
evaluating the image of the meniscus region and the image of the non-meniscus region by different evaluation methods to evaluate a state of the cell included in the captured image.

20. A non-transitory computer readable recording medium storing a cell image evaluation program causing a computer to function as a cell image evaluation device, the function comprising:
determining whether a captured image obtained by capturing an inside of a container that contains a cell is an image obtained by capturing a meniscus region within the container or an image obtained by capturing a non-meniscus region within the container; and evaluating the image of the meniscus region and the image of the non-meniscus region by different evaluation methods to evaluate a state of the cell included in the captured image.

* * * * *